US00PP30895P2

(12) United States Plant Patent
Boeder

(10) Patent No.: US PP30,895 P2
(45) Date of Patent: Sep. 24, 2019

(54) ***DIANTHUS* PLANT NAMED 'A12231-0'**

(50) Latin Name: *Dianthus gratianopolitanus*
Varietal Denomination: A12231-0

(71) Applicant: Armada Young Plants, De Lier (NL)

(72) Inventor: Mark Boeder, The Hague (NL)

(73) Assignee: ARMADA YOUNG PLANTS, The Hague (NL)

( * ) Notice: Subject to any disclaimer, the term of this patent is extended or adjusted under 35 U.S.C. 154(b) by 0 days.

(21) Appl. No.: 15/998,813

(22) Filed: Aug. 16, 2018

(51) Int. Cl.
*A01H 5/02* (2018.01)
*A01H 6/30* (2018.01)

(52) U.S. Cl.
USPC ..... Plt./272

(58) Field of Classification Search
USPC ..... Plt./263.1, 272, 281
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Dianthus* plant named, 'A12231-0', that is characterized by its flowers that are pink in color with a white center, its floriferous blooming habit and its compact plant habit that is suitable for groundcover use.

2 Drawing Sheets

Botanical classification: *Dianthus gratianopolitanus.*
Variety denomination: 'A12231-0'.

CROSS REFERENCE TO A RELATED APPLICATION

This application is co-pending with a U.S. Plant Patent Application filed for a plant derived from the same breeding program that is entitled *Dianthus* Plant Named 'A12228-0' (U.S. Plant patent application Ser. No. 15/998,814).

BACKGROUND OF THE INVENTION

The present invention relates to a new and distinct cultivar of an interspecific hybrid *Dianthus* plant, known as *Dianthus* 'A12231-0' and will be referred to hereinafter by its cultivar name, 'A12231-0'. The new cultivar represents a new herbaceous perennial grown for landscape use.

The new cultivar arose from an ongoing breeding program in De Lier, The Netherlands with the goal of developing new cultivars of *Dianthus* with compact plant habits and prolific flowering in a range of flower colors. 'A12231-0' originated as a seedling that arose from seed planted from open pollination of 'Dianturi Twinkle' (not patented). 'A12231-0' was selected as a single unique plant in April of 2015 from amongst the resulting seedlings.

Asexual propagation of the new cultivar was first accomplished using stem cuttings in April of 2015 in De Lier, The Netherlands. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'A12231-0' as a unique and distinct cultivar of *Dianthus.*

1. 'A12231-0' exhibits flowers that are pink in color with a white center.
2. 'A12231-0' exhibits a prolific blooming habit.
3. 'A12231-0' exhibits a compact plant habit; suitable as a groundcover.

The parent plant, 'Dianturi Twinkle', differs from 'A12231-0' in having a less compact plant habit with a less prolific blooming habit. 'A12231-0' can be most closely compared to the *Dianthus* cultivars 'Kahori' (not patented) and 'A12228-0'. 'Kahori' differs from 'A12231-0' in having flowers that are duller pink in color with flower petals that are less overlapping. 'A12228-0' is similar to 'A12231-0' in having a compact plant habit, a prolific blooming habit, and pink flowers but differs from 'A12231-0' in being even more compact with a shorter height and in having flower centers that are whiter in color.

BRIEF DESCRIPTION OF THE DRAWINGS

The accompanying colored photographs illustrate the overall appearance and distinct characteristics of the new *Dianthus*. The photographs in the figures were taken of a plant one year in age as grown in a greenhouse in a 17-cm container in De Lier, The Netherlands.

The photograph in FIG. 1 provides a side view of a plant of 'A12231-0' in bloom.

Figure 1:
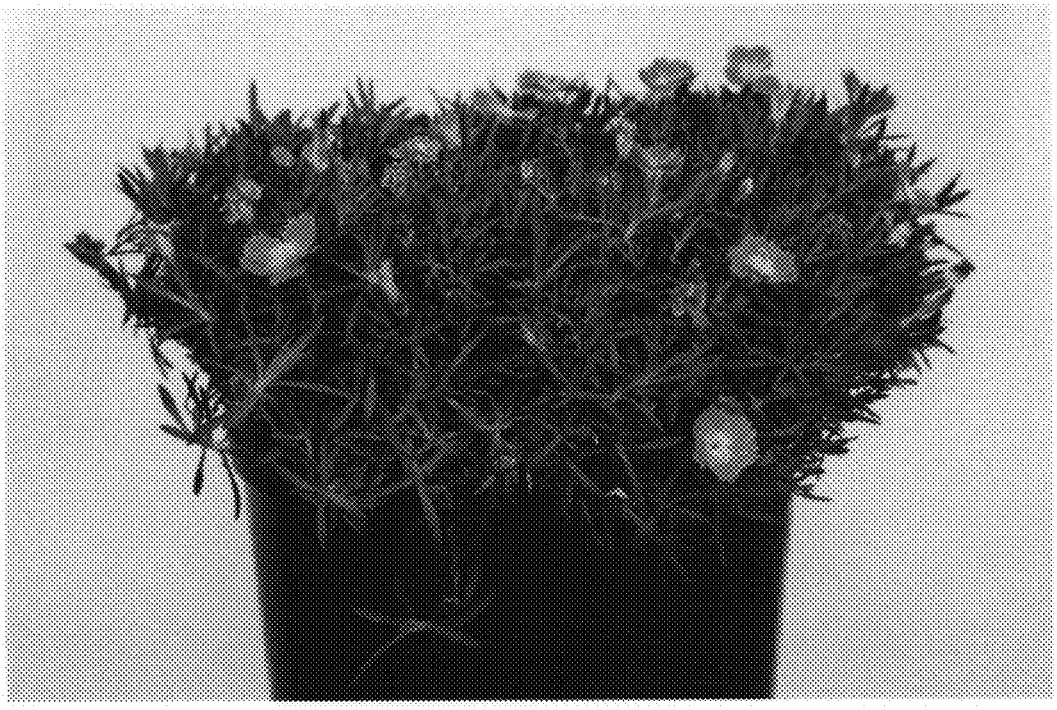
Figure 2:
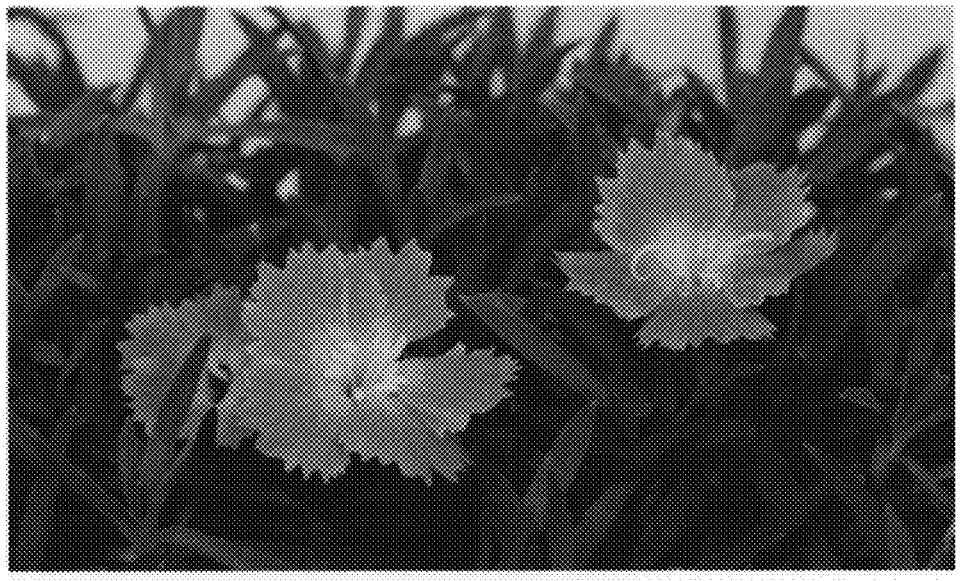

The photograph in FIG. 2 provides a close-up view of the flowers of 'A12231-0'.

Figure 3:
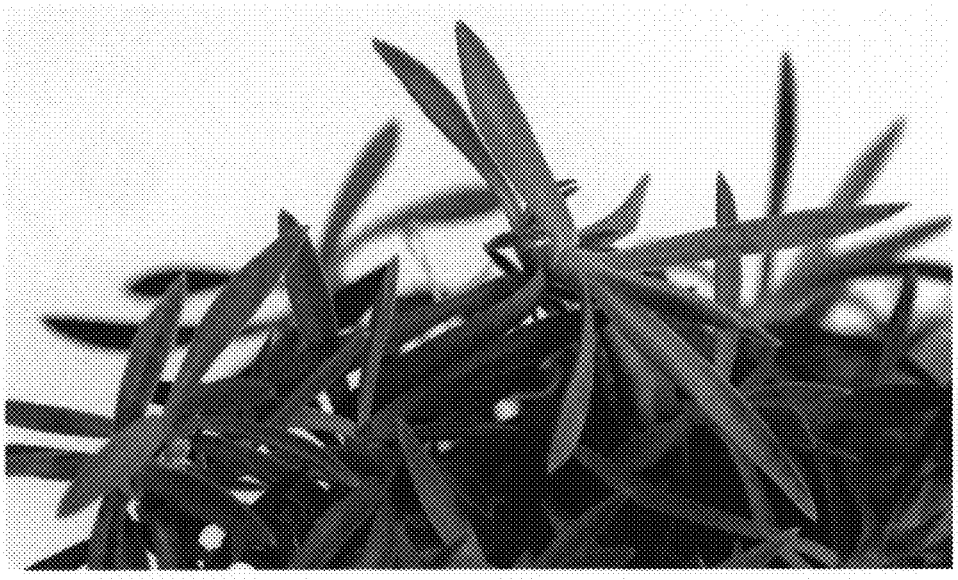

The photograph in FIG. 3 provides a close-up of the foliage of 'A12231-0'.

The colors in the photographs are as close as possible with the digital photography and printing techniques utilized and the color codes in the detailed botanical description accurately describe the colors of the new *Dianthus.*

DETAILED BOTANICAL DESCRIPTION

The following is a detailed description of plants about 1-year-in-age as grown as grown in a greenhouse in 17-cm containers in De Lier, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—Blooms continuously from spring to late summer in The Netherlands.

*Plant type.*—Herbaceous perennial.

*Plant habit.*—Broadly spreading to spreading-upright.

*Height and spread.*—An average of 10.5 cm in height to top of foliar, 11 cm in height to top of floral plane, 28 cm in diameter.

*Hardiness.*—U.S.D.A. Zones 3 to 9.

*Diseases and pests.*—No susceptibility or resistance to diseases or pests has been observed.

*Root description.*—Fibrous and fine.

*Propagation.*—Stem cuttings.

*Root initiation.*—Average of 4 weeks.

*Root development.*—12 to 14 weeks to finish as a young plant from a rooted cutting.

*Growth rate.*—Moderate to high.

Stem description:

*Stem strength.*—Strong.

*Stem aspect.*—Held in multiple angles.

*Shape.*—Rounded.

*Stem size.*—An average of 9.7 cm in height, 1 mm in diameter.

*Stem color.*—Young stems 145B, mature stems 199A to 199B.

*Stem surface.*—Matte.

*Branching habit.*—An average of 12 basal stems and 40 lateral stems per basal stem.

*Internode length.*—Average of 2 mm.

Foliage description:

*Leaf division.*—Simple.

*Leaf shape.*—Oblanceolate, very slightly carinate, very slightly curved.

*Leaf base.*—Decurrent.

*Leaf apex.*—Acute.

*Leaf margin.*—Entire.

*Leaf venation.*—Parallel, color; upper surface NN137A, lower surface 144A.

*Leaf attachment.*—Sessile.

*Leaf arrangement.*—Opposite.

*Leaf surface.*—Both surfaces glabrous, smooth and matte.

*Leaf number.*—An average of 12 (6 pairs) per lateral branch.

*Leaf color.*—Young upper surface; 137A, young lower surface; between 137A and 146B, mature upper surface; NN137A, mature lower surface; 146B.

*Leaf size.*—An average of 3.2 cm in length and 3.5 mm in width.

*Foliage fragrance.*—None.

Flower description:

*Inflorescence type.*—Terminal solitary flowers.

*Lastingness of inflorescence.*—About 10 days, self-cleaning.

*Fragrance.*—Faint, typical *Dianthus* scent.

*Quantity of flowers.*—Average of 65 per plant.

*Flower type.*—Rotate and solitary.

*Flower size.*—An average of 2.4 cm in diameter and 2.1 cm in length.

*Flower buds.*—An average of 7 mm in length and 3 mm in width, elliptic in shape, glabrous, smooth and very slightly glossy surface, color; N138B, base 144B, apex tinged with 181D.

*Peduncle.*—An average of 5 mm in length and 1 mm in diameter, 139D in color, smooth, glabrous and slightly glossy surface, held straight on top of flower stem, moderately strong in strength.

*Pedicel.*—Not present.

*Petals.*—5, rotate, 1 whorl, spathulate in shape, margins irregular dentate, lower half entire, medium undulation, apex irregularly toothed and praemorse, cuneate base, both surfaces velvety, glabrous, slightly velvety, matte, an average of 2.3 cm in length and 1.2 cm in width, color; upper surface when opening 67A, veins 64B, base 145B to 145C, lower surface when opening 63C, veins 63C, base 145B to 145C, upper surface fully open 67A with 155A near petal base and 145B to 145C at very base, lower surface fully open between 63C and 70C, base 145B to 145C, upper surface venation MB, lower surface venation 70C.

*Calyx.*—Rotate, campanulate in shape, an average of 1.3 cm in length and 4.5 mm in diameter.

*Sepals.*—5, rotate, 1 whorl, oblong in shape, entire margin, acute apex, fused base (lower 55% fused into a campanulate shape), an average of 1.1 cm in length and 2 mm in width, smooth, glabrous, matte surface, color; when opening upper surface 144B, apex 144A, when opening lower surface 137B, base 144B, fully open upper surface 144B, towards the apex 144A, fully open lower surface 137B, base 144B.

Reproductive organs:

*Gynoecium.*—2 pistils; an average of 1.7 cm in length, style; NN155D in color, 1.5 cm in length, an average of 1.7 cm in length, stigma; pointed, curved, 150D in color, ovary; 145A in color.

*Androecium.*—Stamens; 10, filament; NN155D in color, an average of 1.4 cm in length, anthers; N170D in color, narrow elliptic, dorsifixed in shape, an average of 1 mm in length, 0.5 mm in width, pollen; low in quantity, 155A in color.

*Fruit and seed.*—Not observed to date.

It is claimed:

1. A new and distinct cultivar of *Dianthus* plant named 'A12231-0' as herein illustrated and described.

* * * * *